United States Patent [19]

Godfraind et al.

[11] 4,376,117

[45] Mar. 8, 1983

[54] CREATINOL-O-PHOSPHATES HAVING THERAPEUTICAL ACTION

[75] Inventors: Théophile Godfraind, Brussels, Belgium; Paolo Ghirardi, Milan, Italy; Giorgio Ferrari, Milan, Italy; Cesare Casagrande, Milan, Italy

[73] Assignee: Simes S.p.A., Milan, Italy

[21] Appl. No.: 198,263

[22] Filed: Oct. 17, 1980

[30] Foreign Application Priority Data

Oct. 26, 1979 [IT] Italy ................. 26854 A/79

[51] Int. Cl.³ .................. A61K 31/66; C07F 9/08
[52] U.S. Cl. ........................... 424/211; 260/944
[58] Field of Search ............ 260/944, 987; 424/211

[56] References Cited

U.S. PATENT DOCUMENTS 3,016,399  1/1962  Debay ........................... 260/945
4,039,636  8/1977  Claus et al. ..................... 260/987

FOREIGN PATENT DOCUMENTS 6401 of 0000 France.

OTHER PUBLICATIONS

Synthesis and Chemical Properties of N- and O-Phosphorylated Derivatives of Creatinol, (1979), pp. 1446-1449.

Primary Examiner—Anton H. Sutto
Attorney, Agent, or Firm—Cushman, Darby & Cushman

[57] ABSTRACT

The magnesium salt of creatinol-O-phosphate, having the formula:

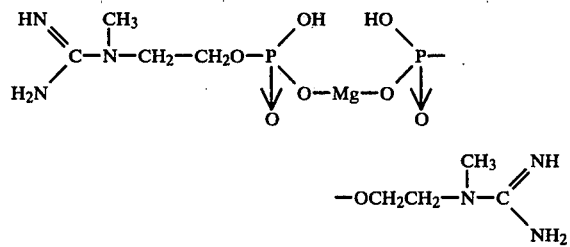

is useful in the treatment and in the prevention of the myocardiac infarction.

The preparation of the above magnesium salt takes place by reacting creatinol-O-phosphate, as a water solution, with a reactive magnesium compound.

The magnesium salt according to the invention may be obtained in either anhydrous or hydrated form and is useful for the preparation of the normal pharmaceutical formulations for the administration by oral and parenteral route.

7 Claims, 1 Drawing Figure

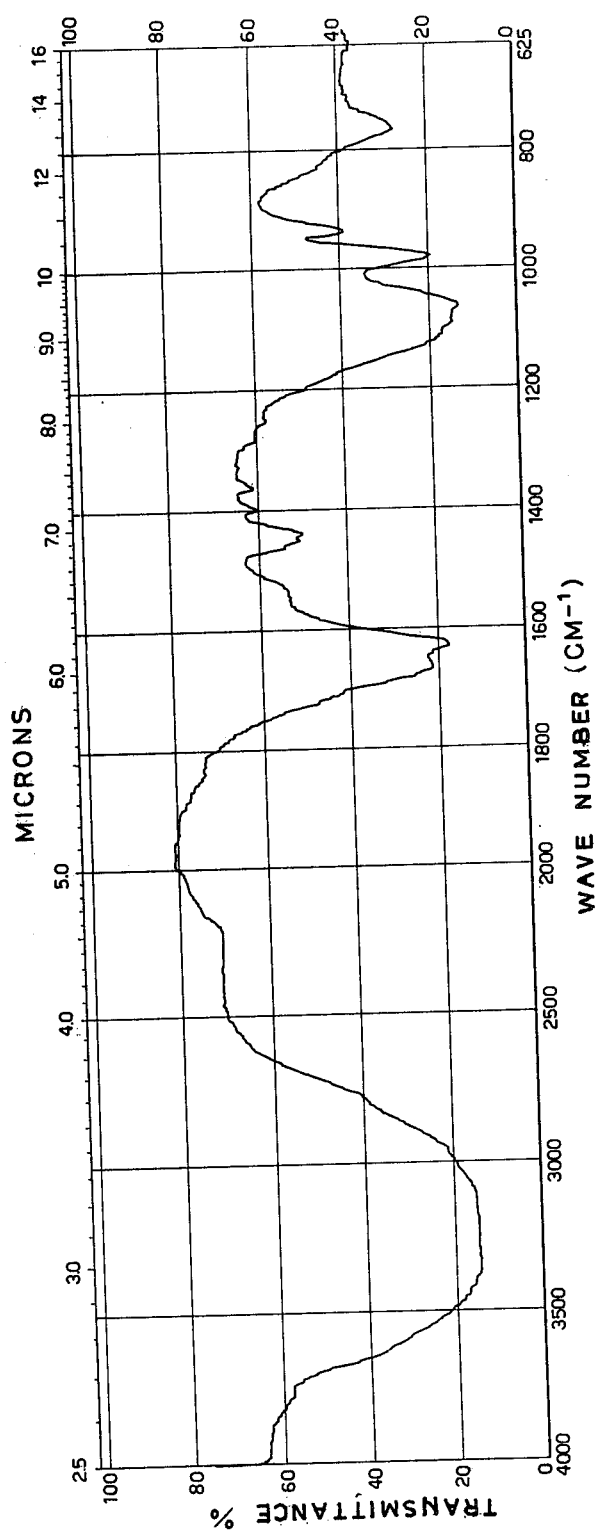

CREATINOL-O-PHOSPHATES HAVING THERAPEUTICAL ACTION

The present invention relates to a novel active principle, useful for the prevention and the therapy of the myocardiac infarction, comprising a derivative of creatinol-O-phosphate, to a process for the preparation of the said derivative of creatinol-O-phosphate, to the pharmaceutical compositions containing the subject active principle and to the therapeutical methods using these pharmaceutical compositions.

The creatinol-O-phosphate

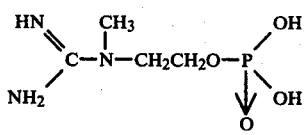

in the free form or also as sodium salt, has been proposed for the treatment of the cardiovascular diseases, amongst which are coronary insufficiency and the cor pulmonale (right heart failure). The pharmacological research work demonstrated that the creatinol-O-phosphate is distinguished with respect to the class of beta-blocking agents and from that of the calcium antagonists, recommended for such a therapeutical use. It is different not only under the pharmacological point of view, but also because it has no side effects such as the negative inotropic action and the atrial ventricular block.

In fact, it has been assessed that the creatinol-O-phosphate causes a positive inotropic effect in the anoxic heart. It has been furthermore demonstrated that the creatinol-O-phosphate causes the number and the surface extension of the ischemic lesions, as induced by the subcutaneous injection of isoprenaline in the rat, to be reduced. Such an effect has been confirmed in the human being since it has been assessed that the creatinol-O-phosphate causes the CPK release in the blood to be reduced, it having also reducing action on the arrithmic episodes occurring in patients suffering from myocardiac ischemia.

It has been now found the magnesium salt of the creatinol-O-phosphate, having the formula (2):

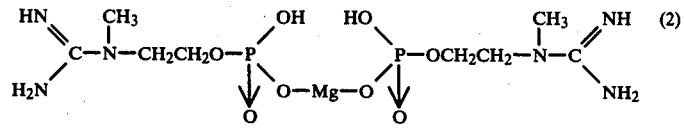

is characterized, with respect to the creatinol-O-phosphate, by its elective action in the treatment and in the prevention of the myocardiac infarction.

These therapeutical uses are based on the pharmacological experiments and, particularly, are confirmed by the tests related to the necrosis as caused by experimentally induced myocardiac ischemia.

For this test, two month aged rats, having an approximate weight of 220 g, have been used. The animals were treated with dosages of 2 mg/kg both of the sodium salt of the creatinol-O-phosphate and of the magnesium salt of creatinol-O-phosphate. The active principle was intraperitoneally injected 4 hours before the subcutaneous injection of isoprenaline (namely of the substance inducing the myocardiac ischemia) at the dosage of 30 mg/kg. The animals were isolated in a room at the temperature of 20° C. and received water and food ad libitum. 24 hours after the injection of isoprenaline, the animals were sacrificed by a blow against their head and subsequent bleeding. The heart was removed and fixed in neutral formal. It was cutted in two parts according to a front section including the two atria, the ventricles and the interventricular septum.

The two segments were coated with paraffin.

In view of the morphometric study, each part was cutted into three sections, having a thickness of 6 microns, at regular intervals, whereby each heart was thus divided into 6 segments.

The several sections were coloured with hematoxylin and zinc saffron.

Each section was reproduced as a photographic picture of 18×25 cm size. Two independent observers examined the randomized sections and marked the reaction areas onto the photographic picture of the section. The number of reaction areas was evaluated at the apex as a percentage of its total surface.

Moreover, the necrotized cells at the apex were counted and their number was expressed as a percent of the surface unit of the reticle used for the morphometry. For each treatment, namely for isoprenaline at the dose of 30 mg/kg either alone, or preceeded by a pre-treatment with sodium creatinol-O-phosphate (2 mg/kg) or with magnesium creatinol-O-phosphate (2 mg/kg), the tests were carried out on groups of 6 rats. The results reported in the following table were found:

TABLE

| | No. of infiltration focuses | Damaged surfaces at apex | Necrotized cells for surface unit |
|---|---|---|---|
| isoprenaline (30 mg/kg) | 38.8 | 20 | 1.1 |
| isoprenaline (30 mg/kg) + sodium creatinol-O—phosphate (2 mg/kg) | 27.7 | 11.5 | 0.75 |
| isoprenaline (30 mg/kg) + magnesium creatinol-O—phosphate (2 mg/kg) | 27.9 | 8.1 | 0.38 |

It is to be noted that by a statistical analysis carried out according to the Student test:

(1) as regards the number of infiltration focuses and the percentage of damaged surface at the apex, the difference between the group treated with isoprenaline alone and the group treated with magnesium or sodium salts of creatinol-O-phosphate is significant ($P<0.05$ and $P<0.05$, respectively);

(2) as regards the number of necrotized cells per surface unit, there is a significant difference not only between the rats previously treated with salts of creatinol-O-phosphate and the rats treated with isoprenaline only, but also a highly significant difference ($P<0.001$)

exists between the rats previously treated with magnesium creatinol-O-phosphate and those treated with sodium creatinol-O-phosphate.

To sum up, it is experimentally demonstrated that the magnesium creatinol-O-phosphate, with respect to the cardiac lesion induced by the isoprenaline, has the same effect as shown by the sodium creatinol-O-phosphate as regards the number of infiltration focuses and their surface area at the apex, but its specific effect on the cell necrosis is surprisingly and exceedingly greater than that of the sodium salt. The evidence thereof is given by the fact that the number of necrotized cells is far lower in the rats pre-treated with magnesium creatinol-O-phosphate than in those pre-treated with sodium creatinol-O-phosphate.

In view of the pharmacological properties above referred to and particularly of the fact that the magnesium salt of creatinol-O-phosphate is capable of reducing the number of necrotized cells in a definitely better way than the corresponding sodium salt, the magnesium salt is indicated for a novel and important therapeutical use in the treatment of the myocardiac infarction.

It has been, in fact, demonstrated that the cariogenic shock (always mortal) occurs when the 40% of the myocardiac mass is destroyed by the reaction following the infarction. It has been, furthermore, demonstrated that the area encompassing the focus perfused by the thrombotic arteria shows a reaction of ischemic type which evolves toward the myocardiac necrosis within 18–24 hours after the infarction. If it is not possible to usefully protect the thrombotic arteria, because the vascularization is eliminated, it has been found that there is the possibility of modifying the importance of the reaction area evolving toward the ischemia and encompassing the area in which the infarction occurred.

Such a modification may consist either in an aggravation, in the case of the action of catecholamines, or in a reduction, when glucose-insulin-potassium are administered by perfusion, thus promoting the reactions of anaerobic glycolysis. It has been suggested that the creatinol-O-phosphate intervenes, at the intracellular level, on the reactions of anaerobic glycolysis.

Thus the specific anti-necrotic effect as induced by the magnesium salt of the creatinol-O-phosphate permits a particularly important therapeutical action to be obtained by this novel active principle; it can be used either in the intensive treatment units, by oral or intermuscular way, or preferably for the administration by continuous intravenous perfusion; it can also be used as first aid drug for the physician upon a cardiac infarction is diagnosed and, in this case, it is preferably administered by intravenous or intermuscular injection.

The novel active compound shall also be useful for preventive purpose, and to this end it shall be administered by oral route to the patients suffering from myocardiac ischemia in order to avoid, before its occurrence, the reactive ischemia which gives place to particularly serious necrosis in the patients already suffering from a first infarction.

It is lastly to be noted a not negligible advantage of the magnesium creatinol-O-phosphate over the sodium salt, namely that of avaiding the supplementing of sodium ions, the latter being always objectionable for patients having a cardiac insufficiency.

The novel magnesium salt of the creatinol-O-phosphate of the present invention is prepared by reacting creatinol-O-phosphate with a reactive derivative of magnesium, of the group comprising magnesium hydroxide, oxide, salts with weak acids, like carbonic acid and carboxylic acids, such as acetic, propionic and butyric acids.

In the preferred embodiment it is prepared by adding magnesium acetate to a water solution of creatinol-O-phosphate and then diluting the solution with ethyl alcohol; the resulting precipitated salt is dried at 50° C. under reduced pressure and contains about 30% of crystallization water; the latter can be removed by extended drying at 100° C. and under reduced pressure.

There is obtained the magnesium salt of creatinol-O-phosphate in the anhydrous form. The chemical analysis of the resulting anhydrous salt (Mg 5.8%; P 14.9%; N 20.2%) corresponds to the formula (2) above and the I.R. spectrum is that shown in the enclosed drawing.

Both the hydrated and the anhydrous forms can be used in the pharmaceutical preparations, depending from the characteristics of the pharmaceutical preparations themselves; the hydrated form is preferably used, owing to its greater dissolving rate in water, when pharmaceutical preparations characterized by ready solubility are desired. However the dosages are preferably referred to the anhydrous form, as already done as regards the dosages cited in the hereinabove discussion of the comparison pharmacological tests.

For the foreseen therapeutical use, the magnesium salt of creatinol-O-phosphate can be prepared in suitable formulations and doses. It can be formulated for the oral use in tablets, capsules, granules, suspension or solutions which permit the administration of unit dosages of between 100 and 500 mg., the administration being possibly repeated several times a day; three daily administrations are preferred, but a higher number of administrations is possible, thanks to the lack of toxicity of the drug.

It can also be formulated for the parenteral use both in form of suspension or solution for intermuscular administration and in form of solutions for intravenous administration; in this case the single doses shall be of between 100 and 200 mg and the administration can be repeated three or more times for each day.

The novel compound can be furthermore, suitably formulated for the dissolving or dilution in solutions to be used for the intravenous perfusion, such as physiological solution of sodium chloride or the 5% glucose solution; in this case the doses shall be calculated, both suitably varying the concentration of the drug, and varying the perfusion rate, so as to carry out the administration of doses of 0.5–3 mg/kg per minute.

The pharmaceutical preparations above referred to are prepared by using suitable excipients, diluents, dispersants and surface active agents; there can be contained the magnesium salt of creatinol-O-phosphate as the only active ingredient, or other active principles, which may usefully integrate the therapeutical effect, may be present.

The following examples have explanatory non limiting purpose as regards the subject of the invention.

EXAMPLE 1

120 g of creatinol-O-phosphate are dissolved at 50° C. in 600 mls of water; the thus obtained solution is supplemented with 174 g of magnesium acetate tetrahydrate as a solution in 300 mls of water; the mixture is gradually diluted with 1400 mls of ethyl alcohol and maintained under stirring for one hour at room temperature: the magnesium salt of creatinol-O-phosphate is filtered and dried under reduced pressure (50 mm Hg) at 50° C.

There is obtained the product in the hydrated form, containing about 30% of crystallization water.

The hydrated product can be dehydrated by heating to 100° C. under reduced pressure (10 mm Hg). The resulting anhydrous salt has a chemical analysis (Mg 5.8%; P 14.9%; N 20.2%) corresponding to the formula (2) and the I.R. spectrum shown in the enclosed drawing.

EXAMPLE 2

The following ingredients, previously ground as fine powder and sieved, are carefully admixed:

| Magnesium salt of creatinol-O—phosphate (anhydrous form) | kg 25 |
|---|---|
| mais starch | kg 55 |
| polyvinylpyrrolidone | kg 5 |
| magnesium stearate | kg 15 |
| silice gel | kg 25 |
| microcrystalline cellulose | kg 50 |

Upon the admixing is completed, the powder is compressed as large wafers having a diameter of 25 mm; the latter are ground in form of granular rough powder by grinding in a suitable grinder and then compressed again by means of a 10 mm diameter punch to obtain tablets (100,000 tablets as a theoretical yield) of 400 mg weight each and containing 250 mg of magnesium salt of creatinol-O-phosphate.

EXAMPLE 3

10 kg of magnesium salt of creatinol-O-phosphate in anhydrous form are dissolved at 40° C. in 500 l of distilled water "pro iniection"; the solution is filtered through a sterilizing membrane and divided, in a sterile room, in vials, in the amount of 5 mls per vial (theoretical yield: 100,000 vials), which are immediately sealed; there are obtained vials, each containing 100 mg of magnesium salt of creatinol-O-phosphate as a water solution, suitable for intravenous and intermuscular administration.

EXAMPLE 4

Under aseptic conditions, 2.86 kg of magnesium salt of creatinol-O-phosphate, in the hydrated form containing 30% of water, are divided by means of a dosing machine in sterile phials, having a 20 ml capacity, which are immediately sealed with a perforable rubber cop and a locking metal ring.

There are obtained phials (theoretical yield: 10,000 phials), each containing 286 mg of magnesium salt in the hydrated form, equivalent to 200 mg of the corresponding anhydrous form, in a form suitable for the intermuscular and intravenous administration, as a unique dose or for slow intravenous perfusion.

In fact, for example, the dose contained in the phial can be suspended in 3-5 mls of water or of physiological solution of sodium chloride for the intermuscular injection; otherwise it may be dissolved in 10-20 mls of physiological solution of sodium chloride or of 5% glucose solution the intravenous injection; or it may be dissolved, by transferring with a syringe, in 250 or 500 mls of a sodium chloride or glucose solution for perfusion, thus obtaining solutions respectively containing 800 and 400 μg/ml, and suitable for the adminstration at dosages of between 0.5 and 3 mg/min., depending on the preselected concentration and perfusion rate.

What is claimed is:

1. A method for the treatment and the prevention of myocardiac infarction, characterized in that magnesium salt of creatinol-O-phosphate is administered, either orally or parenterally or by intravenous perfusion.

2. A method according to claim 1 comprising administering the magnesium salt of creatinol-O-phosphate by intravenous perfusion dissolved in a physiological solution and at a dosage, by weight referred to the anhydrous form of 0.3-5 mg/minute.

3. Magnesium salt of creatinol-O-phosphate having the formula:

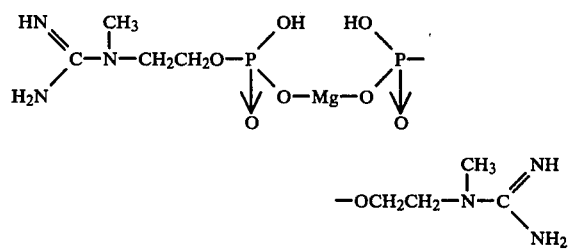

4. Pharmaceutical composition for the treatment and the prevention of the myocardiac infarction, characterized in that it comprises, as the active ingredient, magnesium salt of creatinol-O-phosphate, together with the excipients commonly used for pharmaceutical preparations.

5. Pharmaceutical composition according to claim 4, characterized in that, it is suitable for the oral use and it contains 100-500 mg of magnesium salt of the creatinol-O-phosphate, by weight and referred to the anhydrous form.

6. Pharmaceutical composition according to claim 4, characterized in that, it is suitable for the parenteral use and it contains 100-200 mg of magnesium salt of creatinol-O-phosphate, by weight and referred to the anhydrous form.

7. Pharmaceutical composition according to claim 4, characterized in that, it is suitable for the administration by intravenous perfusion and the magnesium salt of creatinol-O-phosphate is solved in a physiological solution, with a dosage, by weight referred to the anhydrous form, of 0.3-5 mg/minute.